(12) United States Patent
Barkay

(10) Patent No.: US 11,583,468 B2
(45) Date of Patent: Feb. 21, 2023

(54) APPARATUS FOR MASSAGING HUMAN BREAST

(71) Applicant: FEEDWELL LTD, Ramat Yishai (IL)

(72) Inventor: Dov Barkay, Ramat Yishai (IL)

(73) Assignee: FEEDWELL LTD, Ramat Yishai (IL)

( * ) Notice: Subject to any disclaimer, the term of this patent is extended or adjusted under 35 U.S.C. 154(b) by 176 days.

(21) Appl. No.: 16/294,689

(22) Filed: Mar. 6, 2019

(65) Prior Publication Data

US 2019/0240109 A1  Aug. 8, 2019

Related U.S. Application Data

(63) Continuation of application No. PCT/IL2017/051003, filed on Sep. 6, 2017.

(Continued)

(51) Int. Cl.
*A61H 9/00* (2006.01)
*A61H 23/04* (2006.01)
(Continued)

(52) U.S. Cl.
CPC .......... *A61H 9/0078* (2013.01); *A41C 3/005* (2013.01); *A41C 3/0064* (2013.01); *A41C 3/105* (2013.01); *A61H 9/00* (2013.01); *A61H 23/04* (2013.01); *A61M 1/06* (2013.01); *A61M 1/062* (2014.02); *A41B 2400/322* (2013.01); *A61H 2201/0207* (2013.01); *A61H 2201/0228* (2013.01); *A61H 2201/1409* (2013.01);
(Continued)

(58) Field of Classification Search
CPC .. A61H 9/00; A61H 9/0078; A61H 2205/082; A61H 7/00; A61H 23/04; A41C 3/005; A41C 3/0064; A41C 3/105; A41B 2400/322; A61M 1/06; A61M 1/062; A61M 1/064; A61M 1/066; A61M 1/068
USPC ....................................................... 601/151
See application file for complete search history.

(56) References Cited

U.S. PATENT DOCUMENTS

| 2005/0234370 A1 | 10/2005 | Beal et al. | |
| 2006/0270973 A1* | 11/2006 | Chu | ..................... A61H 9/0078 604/74 |

(Continued)

FOREIGN PATENT DOCUMENTS

| CN | 202665930 U | * | 1/2013 |
| CN | 202665930 | | 3/2013 |

(Continued)

OTHER PUBLICATIONS

Translation of CN 202665930. Accessed from Espaceneton Jan. 26, 2021. (Year: 2013).*

*Primary Examiner* — Valerie L Woodward
*Assistant Examiner* — Paige Kathleen Bugg
(74) *Attorney, Agent, or Firm* — Browdy and Neimark, P.L.L.C.

(57) ABSTRACT

The present invention A massaging apparatus for human breast, said apparatus comprised of: an electrical pump, a bra having: at least two inflatable tubes having two opening at their edges integrated at each side of the bra encircling one breast organ, wherein each inflatable tube is connected by T shape connector, wherein through pipe to the electronic pump and control module for controlling the inflation of the tubes; wherein the tube are inflated simultaneous at both edges creating dual simultaneous pressure at different size of the breast organ.

9 Claims, 14 Drawing Sheets

Related U.S. Application Data

(60) Provisional application No. 62/383,776, filed on Sep. 6, 2016.

(51) Int. Cl.
*A61M 1/06* (2006.01)
*A41C 3/00* (2006.01)
*A41C 3/10* (2006.01)

(52) U.S. Cl.
CPC ............. *A61H 2201/165* (2013.01); *A61H 2201/1621* (2013.01); *A61H 2201/1645* (2013.01); *A61H 2205/082* (2013.01)

(56) References Cited

U.S. PATENT DOCUMENTS

| | | | |
|---|---|---|---|
| 2012/0116298 A1* | 5/2012 | Van Schijndel | A61B 5/0533 604/74 |
| 2015/0065994 A1* | 3/2015 | Fridman | A61M 1/068 604/514 |
| 2017/0112983 A1* | 4/2017 | Thorne | A61N 1/322 |
| 2017/0136160 A1* | 5/2017 | Barral | A61M 1/06 |
| 2018/0001002 A1* | 1/2018 | Makower | A61M 1/066 |
| 2018/0326130 A1* | 11/2018 | Thompson | A61M 1/066 |
| 2020/0337938 A1* | 10/2020 | Kumar | A41C 3/04 |

FOREIGN PATENT DOCUMENTS

| | | | | |
|---|---|---|---|---|
| CN | 105326635 A | 2/2016 | | |
| EP | 1992861 A2 * | 11/2008 | ............. | A61H 1/008 |
| WO | 2004026368 A1 | 4/2004 | | |
| WO | 2015029029 A1 | 3/2015 | | |

* cited by examiner

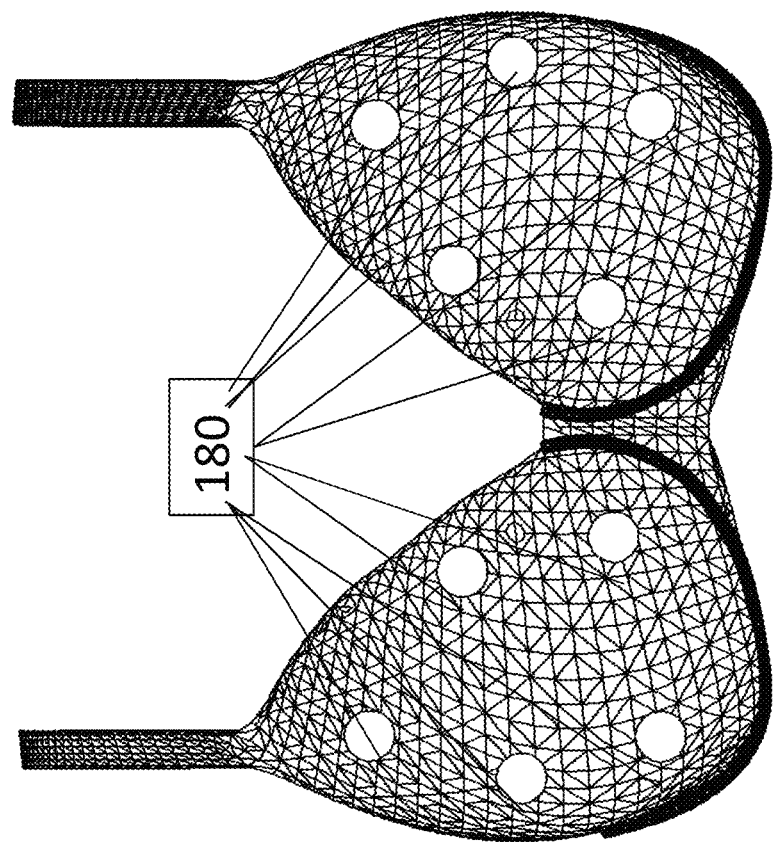
Fig. 8A                    Fig. 8B

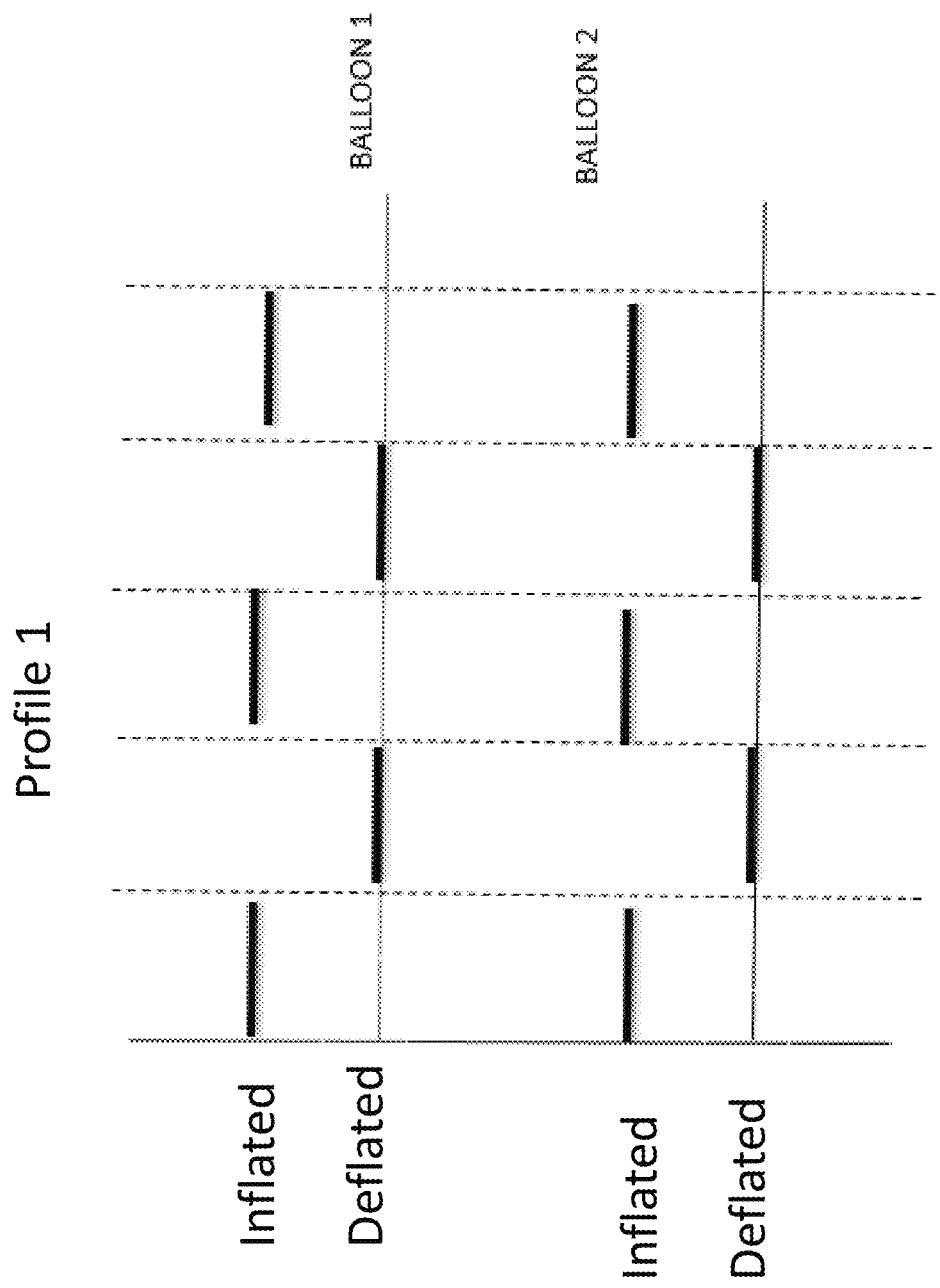

APPARATUS FOR MASSAGING HUMAN BREAST

CROSS REFERENCE TO RELATED APPLICATIONS

This application claims the benefit of the filing date(s) of and, by this reference, incorporates the following applications, in their entirety, into this application: U.S. Provisional Patent Application No. 62/383,776, filed Sep. 6, 2016, and PCT Application number PCT/IL2017/051003, with an international filing date of Sep. 6, 2017, which application designated the United States of America. This application is a continuation of PCT Application number PCT/IL2017/051003.

TECHNICAL FIELD

The present invention relates to the field of wearable devices that can stimulate or apply massage a user's body, specifically wearable bra products that can stimulate or massage human breasts.

BACKGROUND

The benefits of therapeutic breast massage are numerous, and include enhancing the flow of lymphatic fluid in and around the breast and arm-pits region, rehabilitation of scar tissues following surgical procedures, such as breast implants and reconstructive surgery, stimulation of blood circulation, and removal of toxins from the breast area, and strengthening muscle tissue.

SUMMARY OF THE INVENTION

Embodiments of the present invention provide massaging apparatus for a human breast, said apparatus comprising an air pump unit; a bra, having at least an inner and an outer inflatable tube, each having an air inlet and integrated at each side of the bra encircling the breast, wherein each inflatable tube is connected by a connector connected to the air pump; and a control module for controlling the inflation of the tubes, wherein the tubes are inflated at both edges creating dual simultaneous pressure at different location of the breast organ. In some embodiments, a first part of each inflatable tube is relatively thicker than a second part. The air pump unit may concentrate pressure to specific locations by inflating each tube separately. The air pump unit may inflate the inner tube and the outer tube at different times according to a pre-defined protocol, providing movement similar to the sensation of a massage given by a human masseuse.

Heating elements may be integrated as conductive wires and the air pump unit may include output interfaces to electric wires that convey electric power to said heating elements. Vibration elements may be embedded in the bra and the air pump unit, which may include output interfaces to electricity conducting wires, which may convey electric power to said elements vibration elements.

The air pump unit may apply simultaneously a combination of functions of massage, vibration and heating at predefined timing periods. The inflatable tubes may have a restricting film, and the restrictive film may prevent the inflatable tube element from expanding in an isotropic manner. Rings of a restricting film may be spaced around the circumference of the inflatable tube element. The connector may include two air inlets connected to the air pump unit and two pairs of air outlets connected to the outer and inner inflatable tubes, enabling the air pump unit to inflate each tube separately according to a pre-defined protocol.

BRIEF DESCRIPTION OF THE DRAWINGS

The present invention will be more readily understood from the detailed description of embodiments thereof made in conjunction with the accompanying drawings of which:

FIG. 8a shows a schematic perspective view of the massage bra, including vibration elements embedded within the bra, according to an embodiment of the present invention. FIG. 8b shows an example of a vibrating device, according to an embodiment of the present invention.

FIGS. 12A-12C show profiles of inflating the tubes, according to an embodiment of the preset invention.

DETAILED DESCRIPTION

Figure 1:
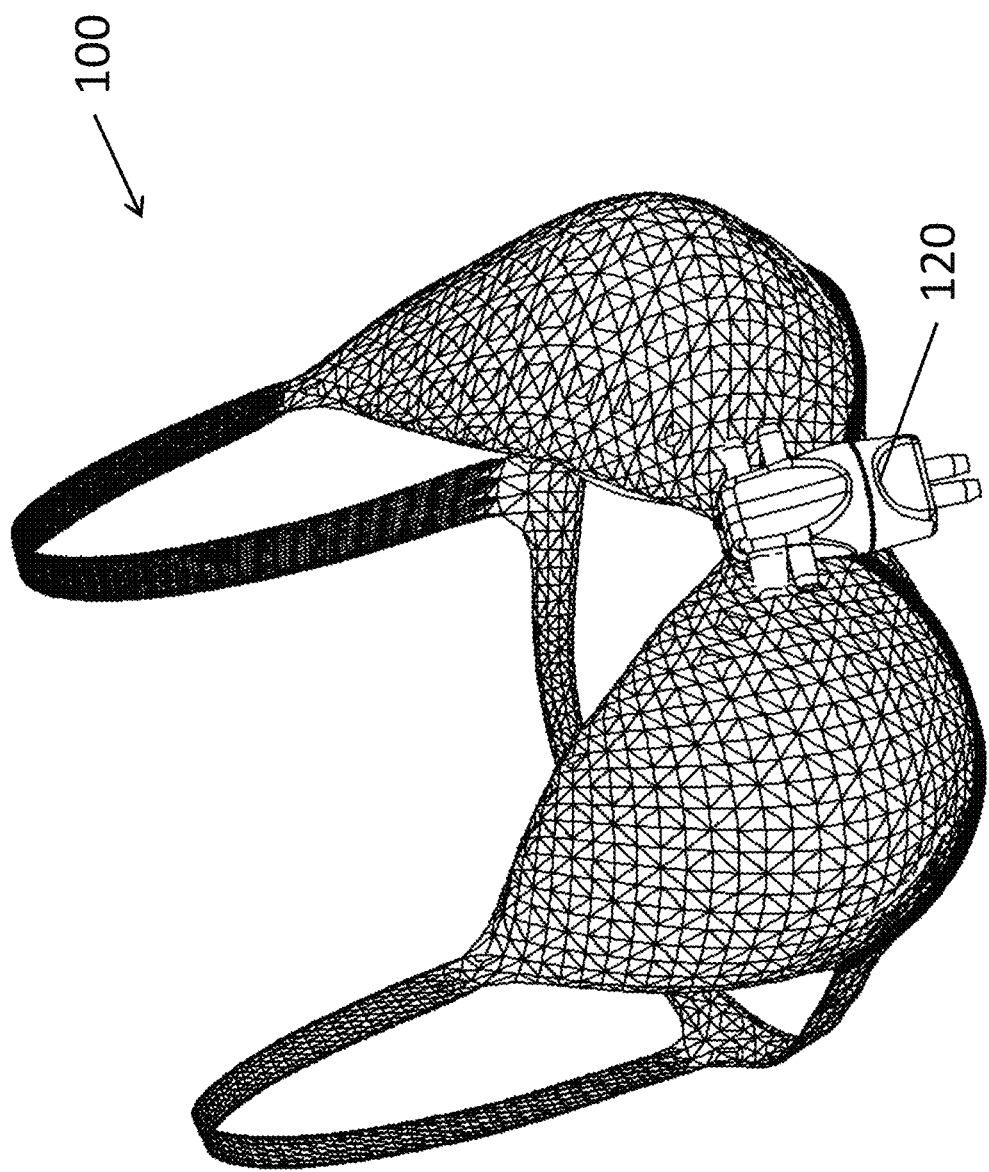
FIG. 1 shows a perspective exterior view of a massage bra, according to an embodiment of the present invention.

It is to be understood that the invention is not limited in its application to the details of construction and the arrangement of the components set forth in the following description or illustrated in the drawings. The invention is applicable to other embodiments or of being practiced or carried out in various ways. Furthermore, the phraseology and terminology employed herein is for the purpose of description and should not be regarded as limiting.

The present invention discloses a massage bra, which is comfortably worn by the user, as any normal bra. According to an embodiment of the present invention, the massage bra applies at least one of the following actions to the user's breasts:

1. Massages breast tissues, by means of embedded inflatable tubes, made of TPU (thermoplastic polyurethane) or latex.
2. Heating of specific regions of the breast, by means of embedded heating elements, and
3. Vibration of specific regions of the breast, by means of embedded vibrating elements.

4. Collects bio-feedback information from different sensors reflecting the effectiveness of the applied actions.

According to an embodiment of the present invention, the actions applied by the massage bra can be manually controlled via a separate control unit.

FIG. 1 shows a perspective exterior view of a massage bra 100, according to one embodiment of the present invention. The massage bra is comfortably worn in a similar fashion to any other normal bra. The present invention is not limited to any particular method of strapping or fitting of the bra onto the user's breasts. The exterior appearance also resembles that of any normal bra, except for the massage bra connector 120, located at the massage bra's frontal side, between the bra cups.

Figure 2:
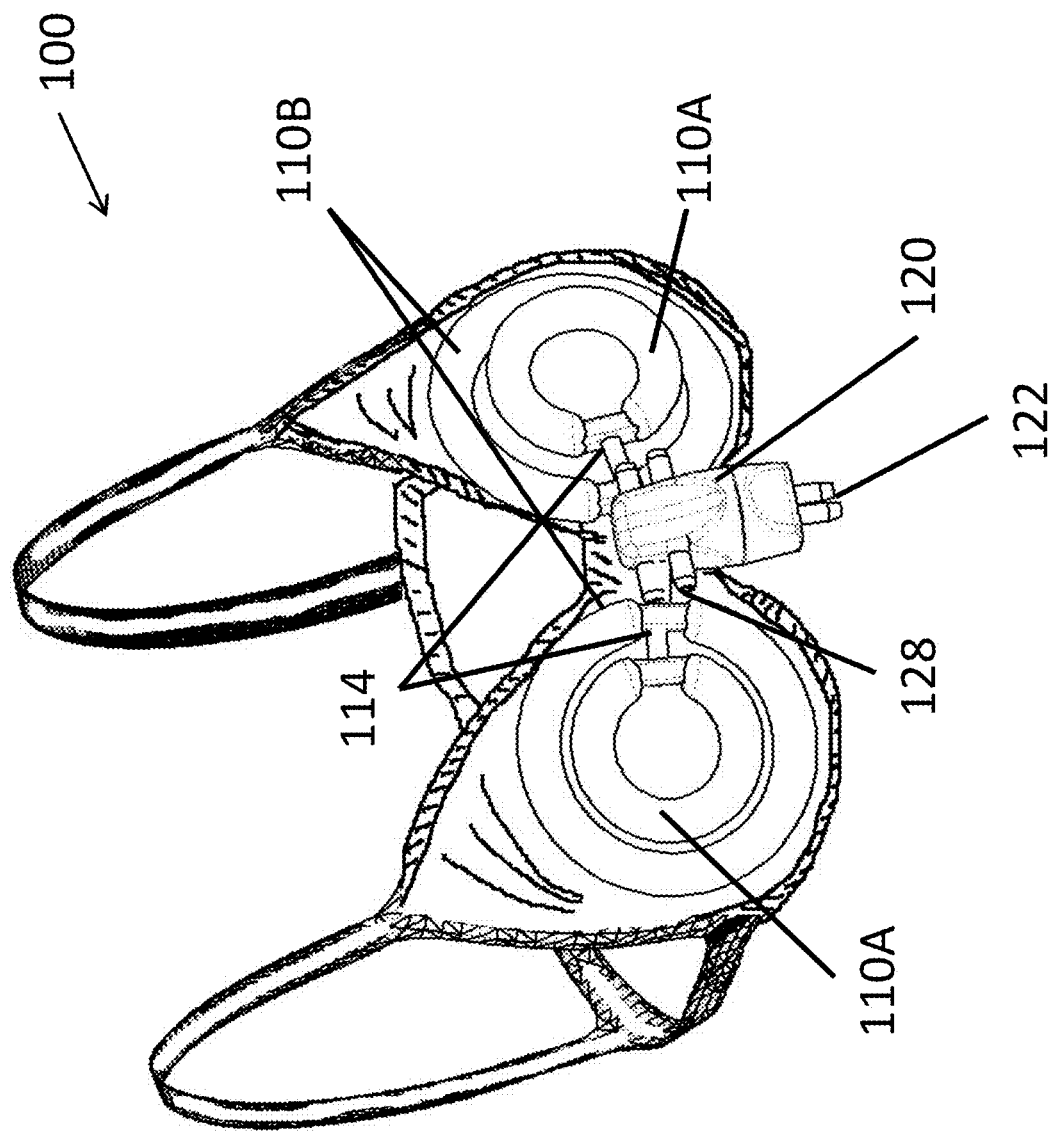
FIG. 2 shows a perspective view of the massage bra, including embedded inflatable tubes, according to an embodiment of the present invention.

FIG. 2 shows a perspective view of the massage bra, revealing a plurality of embedded inflatable tubes, including inner tubes 110A and outer tubes 110B, as implemented according to an embodiment of the present invention. The plurality of inflatable tubes is embedded between the layers of cloth incorporating the bra, and is not visible on the exterior. Each inflatable tube includes at least one tube air inlet 114 that serves to inflate the tube according to its specified design, as described in the following images.

The air is pumped to the tube air inlets from a connector 120, which has connector air inlets 122 and a connector air outlets 128, which are connected to appropriate air inlets on the plurality of inflatable tubes, resulting in the inflation of the tubes. In some embodiments the inlets and outlets have dual plugs for greater reliability.

The plurality of inflatable tubes facilitates the application of localized massage pressure. This property enables the massage bra to concentrate pressure to specific locations, and even apply patterns of movement, similar to the sensation of a massage given by a human masseuse.

Figure 3:
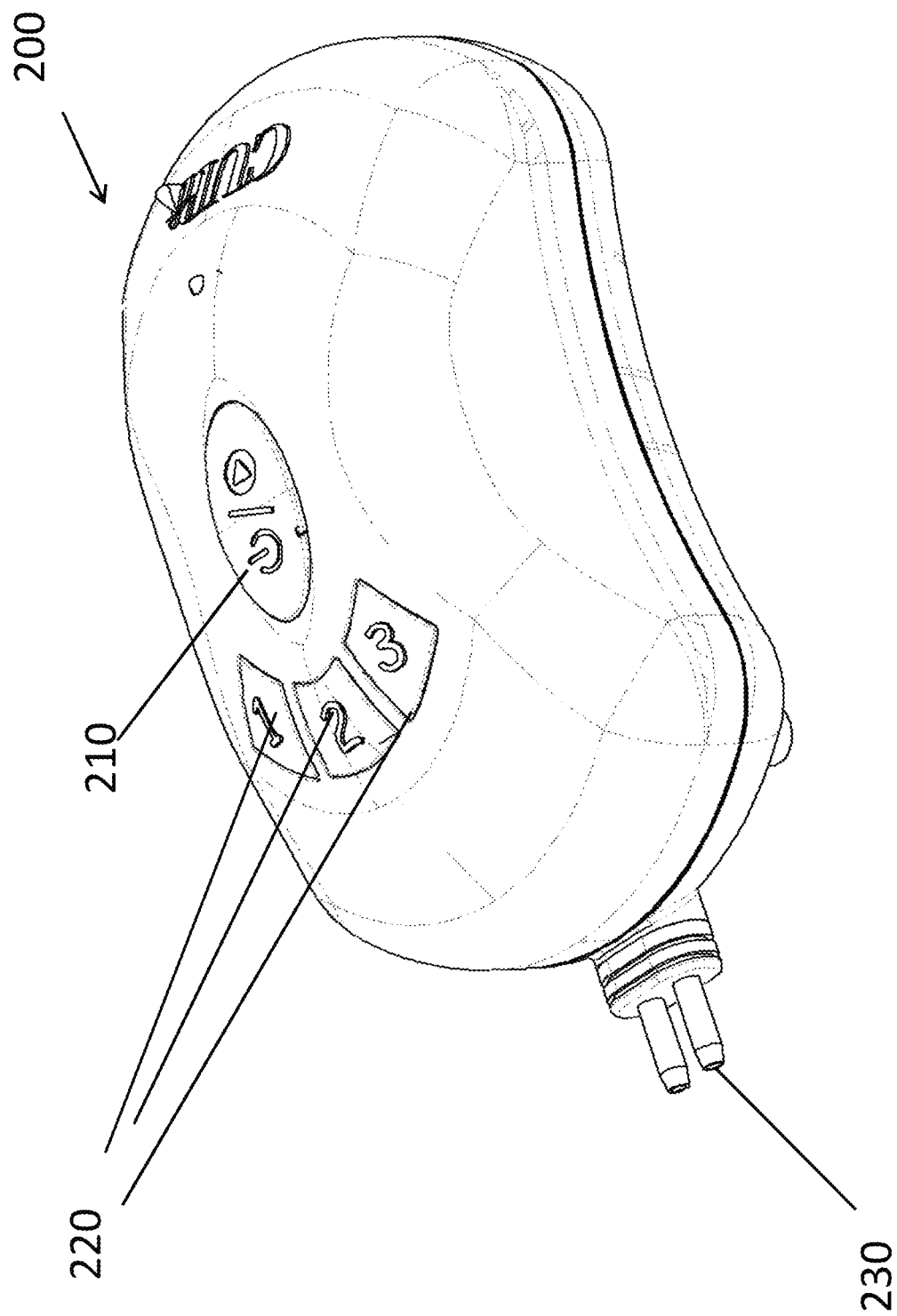
FIG. 3 shows an air pump unit of the massage bra, according to an embodiment of the present invention.

FIG. 3 presents an air pump unit 200 according to an embodiment of the present invention. The air pump unit is designed to:
1. Enable the user to turn the massage bra on or off;
2. supply compressed air to the inflatable tubes embedded in the massage bra;
3. control the heating function of the bra;
4. control the vibration function of the bra; and
5. display and store bio-feedback data accumulated by multiple sensors located within the massage bra, e.g. body temperature, heart rate, skin salinity.

The air pump unit includes a button 210 for turning the apparatus on or off and profile selection buttons 220. Example of profiles that may be selected include:
inflate 110A, then inflate 110B, then deflate 110A and 110B;
inflate 110A and 110B, then deflate 110A and 110B; and
inflate 110A and deflate 110B, then deflate 110A and inflate 110B;

The profile selection buttons also permit selecting additional massage properties, e.g. slow, rapid, shallow, or intense; adjusting the heating function (i.e. warm/cool); adjusting the vibration quality of the massage bra (i.e. stronger/weaker).

Typically the air pump unit also includes a plurality of air outlets 230, conveying compressed air to the massage bra 100

Internal to the air pump unit is generally an air compressor (not shown), which pumps air through the air outlets to the massage bra according to the selected massage profile. Typically, the timing of compression is controlled by a control module, typically a programmable computer microcontroller or by other timing devices known to control air compressors, which is also generally embedded in the air pump unit.

According to an embodiment of the present invention, the air pump unit generally includes electric output interfaces that convey electric power to vibration elements and heating elements embedded within the massage bra 100. The said electric output interfaces may be either incorporated within the air outlets, thus coupling the electric conductors with the air pipes, or as individual wires, conducting electricity on a physically separate route from the air tubes.

The microcontroller generally includes a memory for storing a current configuration, as well as instruction code. The air pump unit may also include a display indicating the current profile and other information, such as acquired bio-feedback data (e.g. a user's heart rate).

Figure 4A:
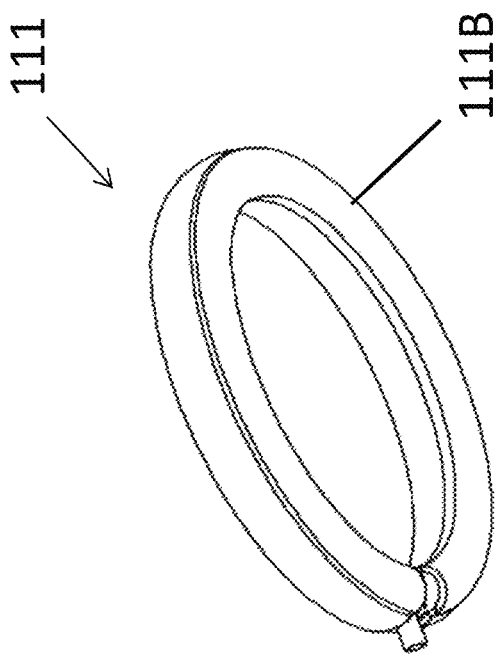
FIG. 4 shows an inflatable tube element, which is embedded within the massage bra, according to an embodiment of the present invention.
Figure 4B:
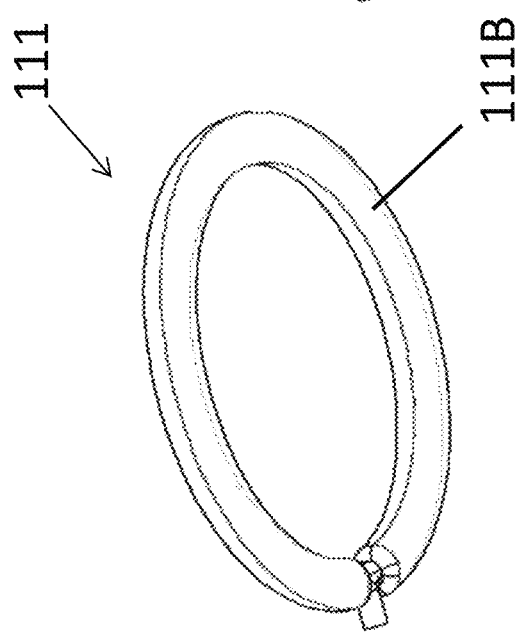

FIGS. 4A and 4B show an inflatable tube 111, embedded in the bra as indicated by tubes 110A or 110B of FIG. 2, according to an embodiment of the present invention. FIGS. 4A and 4B the tube before and after inflation, respectively, according to an embodiment of the present invention.

The inflatable tube 111 includes a restricting film 111B on one side of the inflatable tube element. The restrictive film prevents the inflatable tube element from expanding evenly in all directions and thus applies increased massage pressure in the direction perpendicular to the location of the restrictive film. Alternatively, one side of the tube may be thicker than the other, causing a similar effect of disproportionate inflation.

Figure 5B:
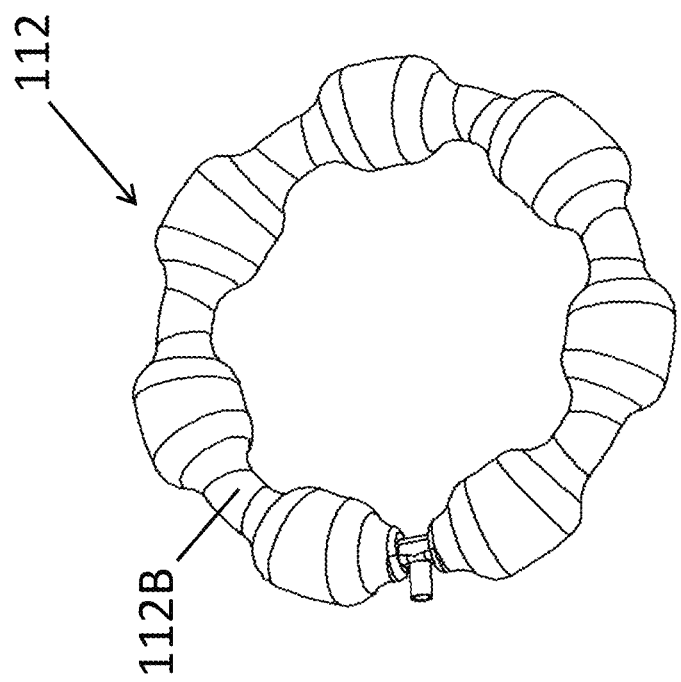
FIG. 5 shows an inflatable tube element, which is embedded within the massage bra, according to an embodiment of the present invention.
Figure 5A:
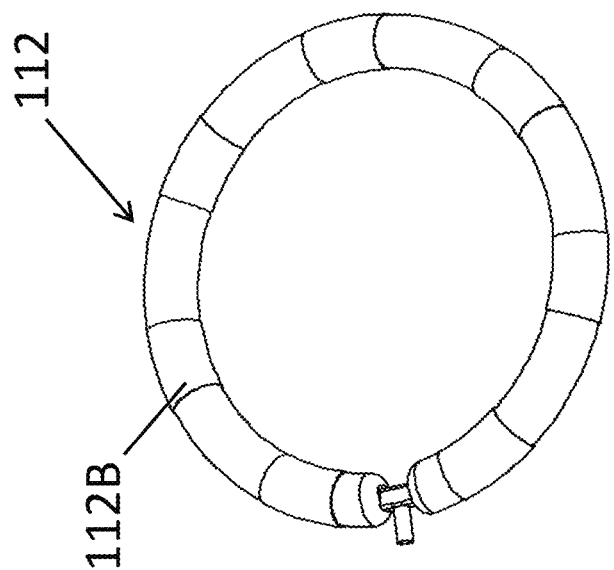

FIGS. 5A and 5B show an inflatable tube 112, embedded in the bra as indicated by tubes 110A or 110B of FIG. 2, according to an embodiment of the present invention. FIGS. 4A and 4B the tube before and after inflation, respectively, according to an embodiment of the present invention.

The inflatable tube 112 includes multiple restricting films 112B encircling various locations of the inflatable tube element. The restrictive films prevent the inflatable tube element from expanding evenly along the entire circumference of the tube. The application of such restrictive film rings forces the inflatable tube element 112 to expand unequally, as in a ring pattern. This enables the concentration of massage pressure to designated locations.

Figure 6B:
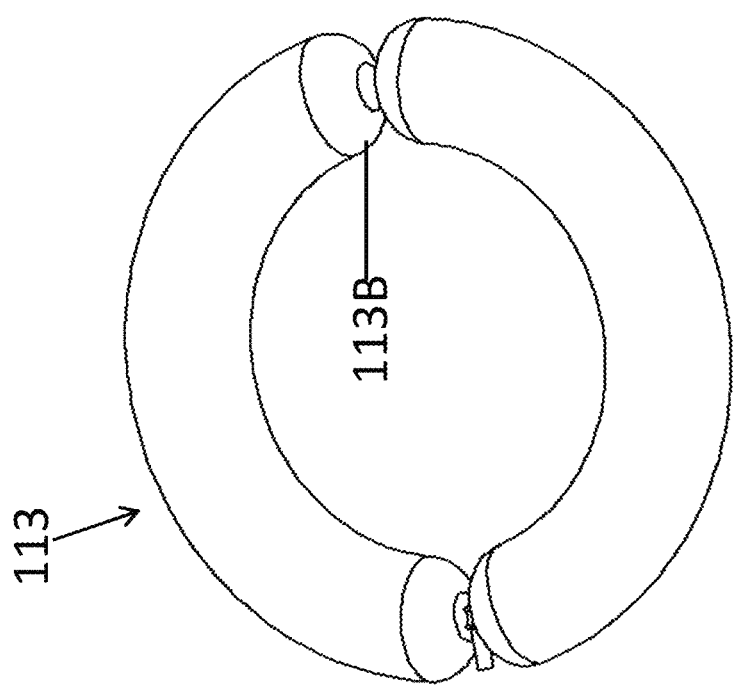
FIG. 6 shows an inflatable tube element, embedded within the massage bra, according to an embodiment of the present invention.
Figure 6A:
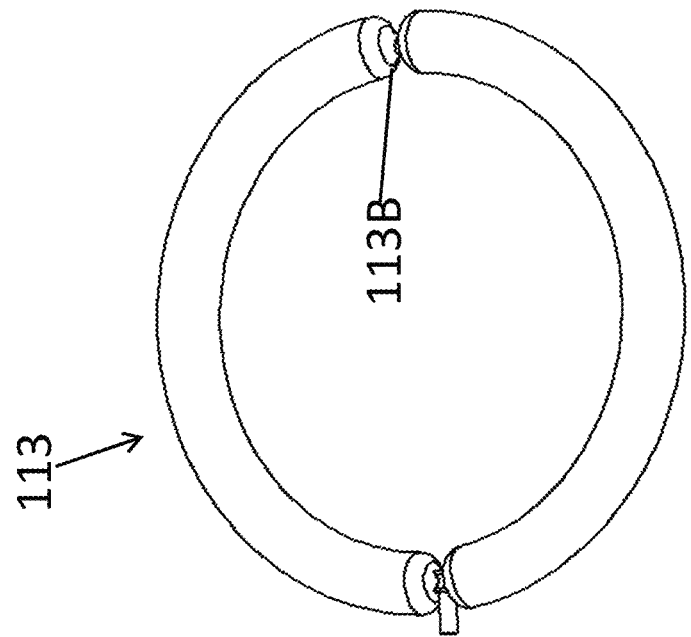

FIG. 6 presents another inflatable tube element 113, which is embedded within the massage bra, before and after the act of inflation, according to an embodiment of the present invention. The inflatable tube 113 differs from inflatable tube elements 110 of FIG. 2 in that a torsion is applied at its middle point 113B, effectively dividing the inflating tube in two. The air inlet may be duplicated such as to separately provide compressed air to each part of the tube. The said configuration enables yet another massage pattern; applying pressure separately to different parts of the user's breasts.

Figure 7:
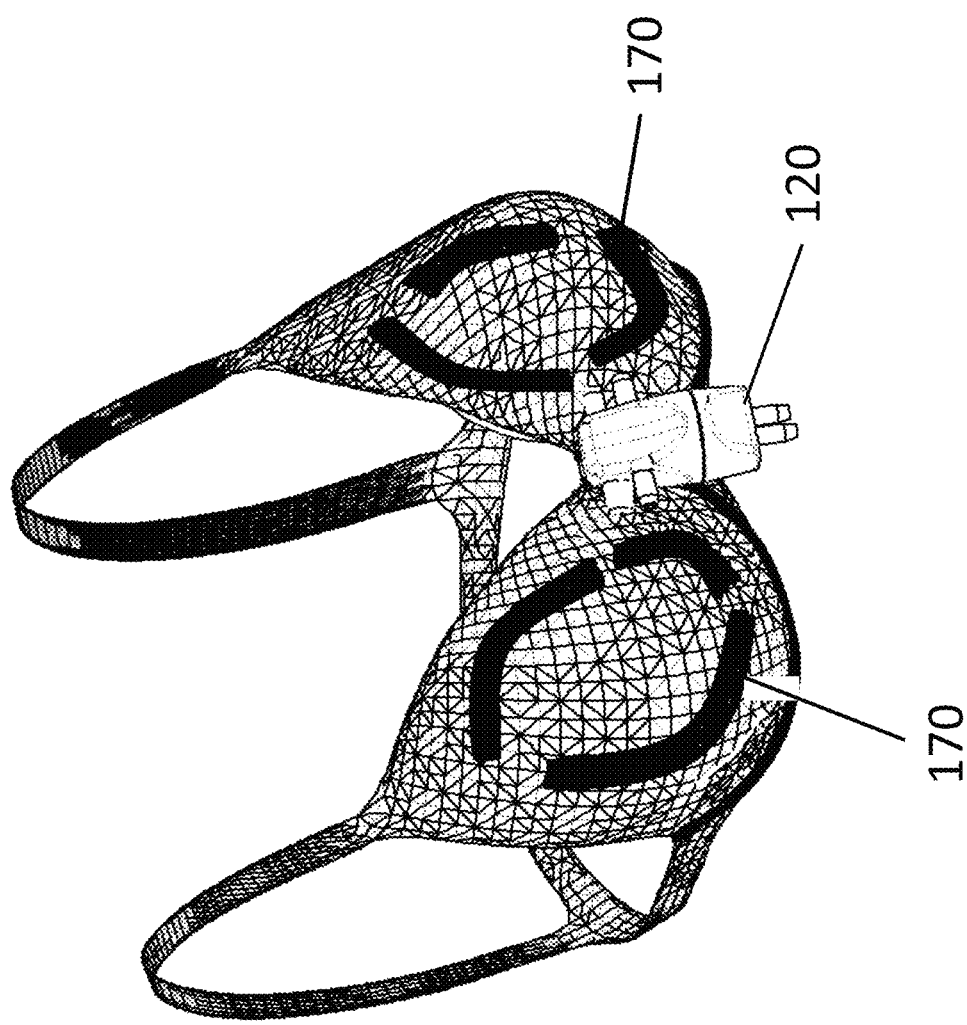
FIG. 7 shows a schematic perspective view of the massage bra, including heat elements embedded within the bra, according to an embodiment of the present invention.

FIG. 7 presents a schematic perspective view of the massage bra, pointing out the location of heating elements 170 embedded within the bra, according to an embodiment of the present invention. The said heating elements 170 may be implemented as conductive wires, drawing their power either from the air pump unit 200 (FIG. 3), or from batteries encased within the massage bra connector 120.

FIG. 8a presents a schematic perspective view of the massage bra, pointing out the location of the vibration elements 180 embedded within the bra, according to an embodiment of the present invention. The said vibration elements may draw their power either from the air pump unit 200, or from batteries encased within the massage bra interface 120. FIG. 8b presents an example of such a vibrating device. This example illustrates an IMC Hot DC 3V 60 mA 9000+/−2000 RPM Phone Coin Flat Vibrating Vibration Motor. Other vibrating devices may be used.

Figure 9:
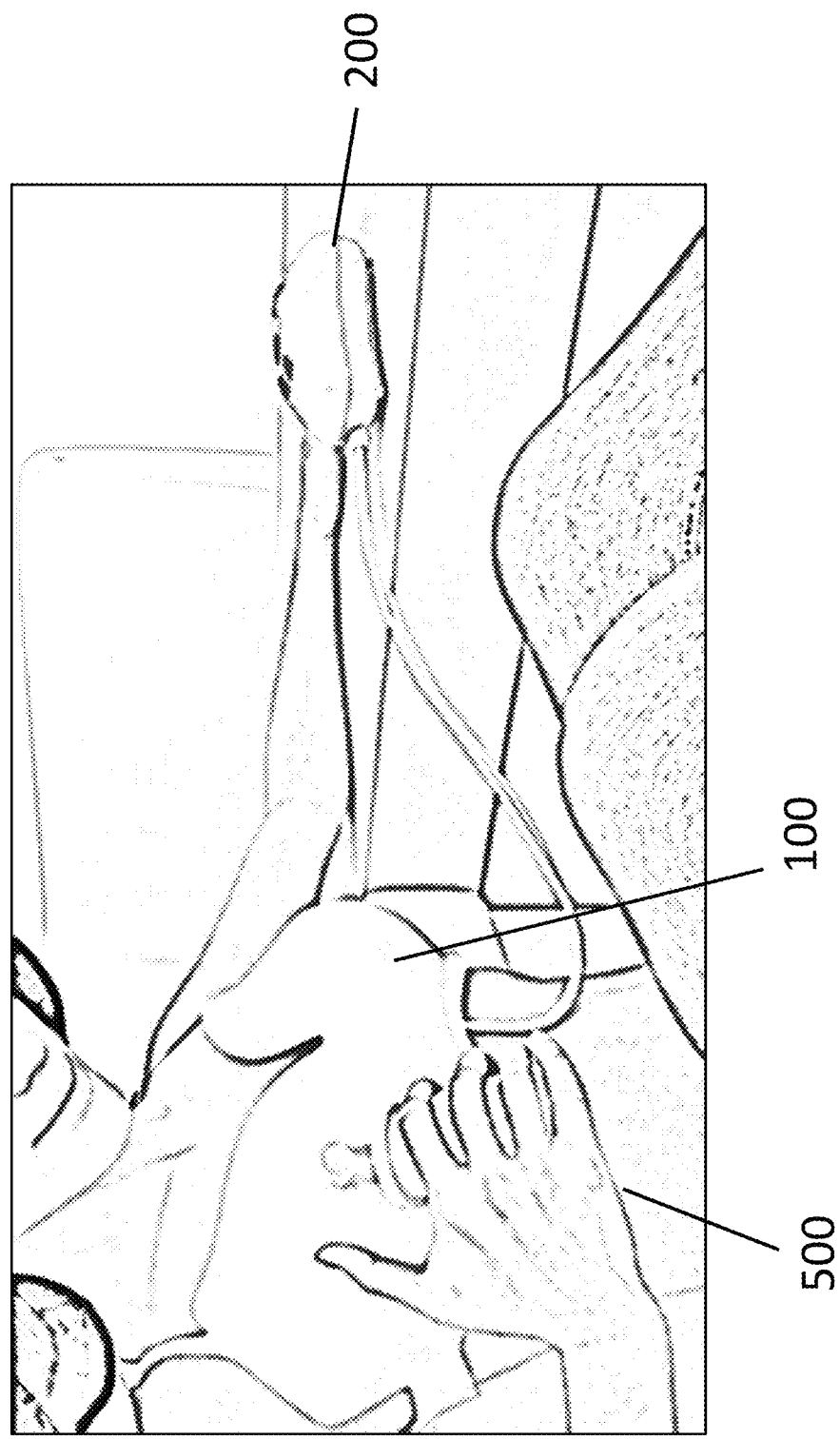
FIG. 9 shows a simulated activation of the massage bra during extraction of breast milk, according to an embodiment of the present invention.

FIG. 9 shows a user 500 operating the massage bra 100, according to an embodiment of the present invention. The user may be simultaneously extracting breast milk. The layered structure of the massage bra enables the exposure of the nipples of the user's breast, whilst maintaining the supportive structure of the massage bra. The air pump unit 200 is shown near the user.

Figure 10:
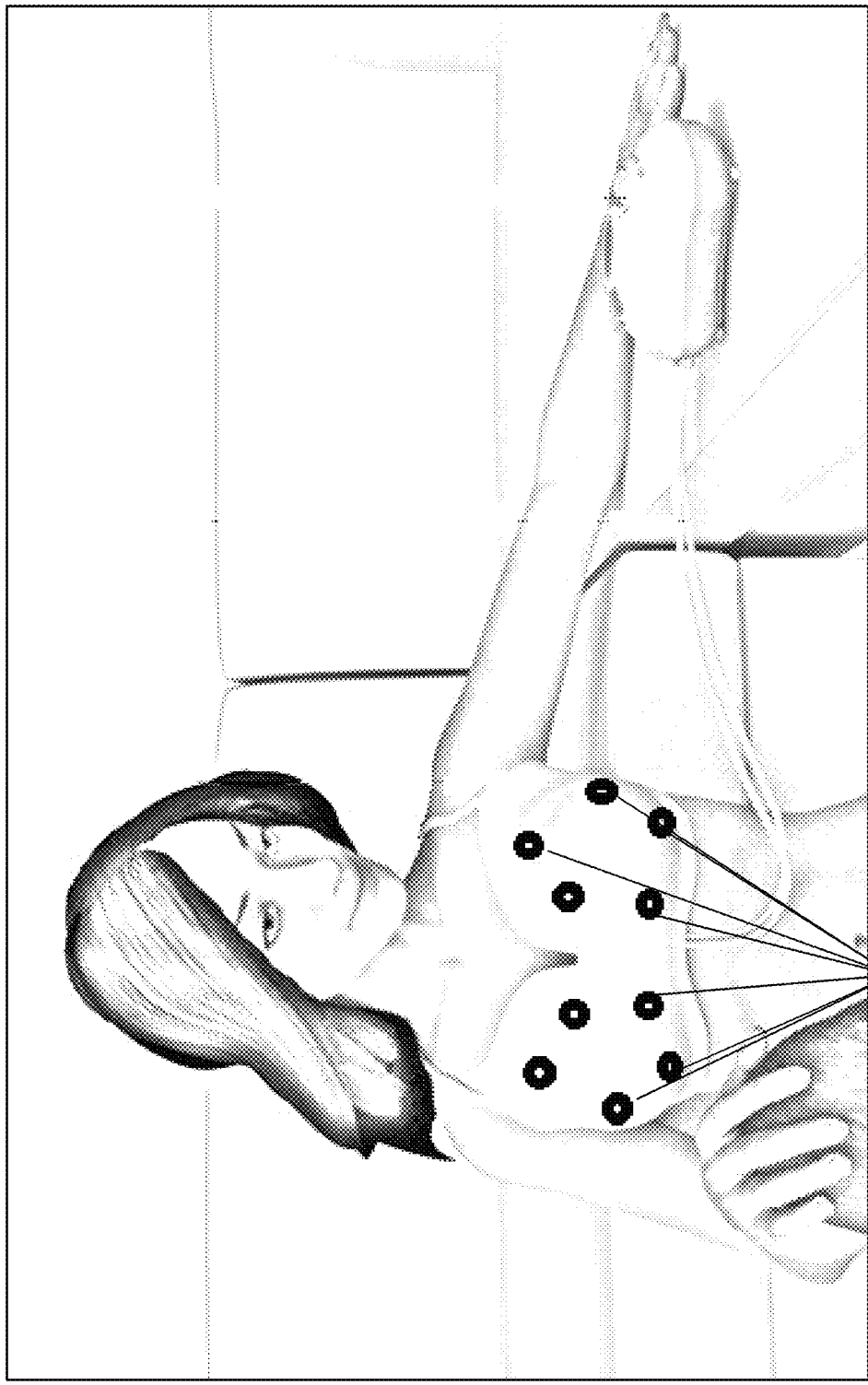
FIG. 10 shows the location of bio-feedback sensors embedded within the massage bra, according to an embodiment of the present invention.

FIG. 10 shows the locations of bio-feedback sensors 190, for making measurements such as body temperature, heart rate, skin salinity, the sensors being embedded within the massage bra 100. The data collected by these sensors may be transmitted to the computational module within the control unit 200, which may also display.

Figure 11:
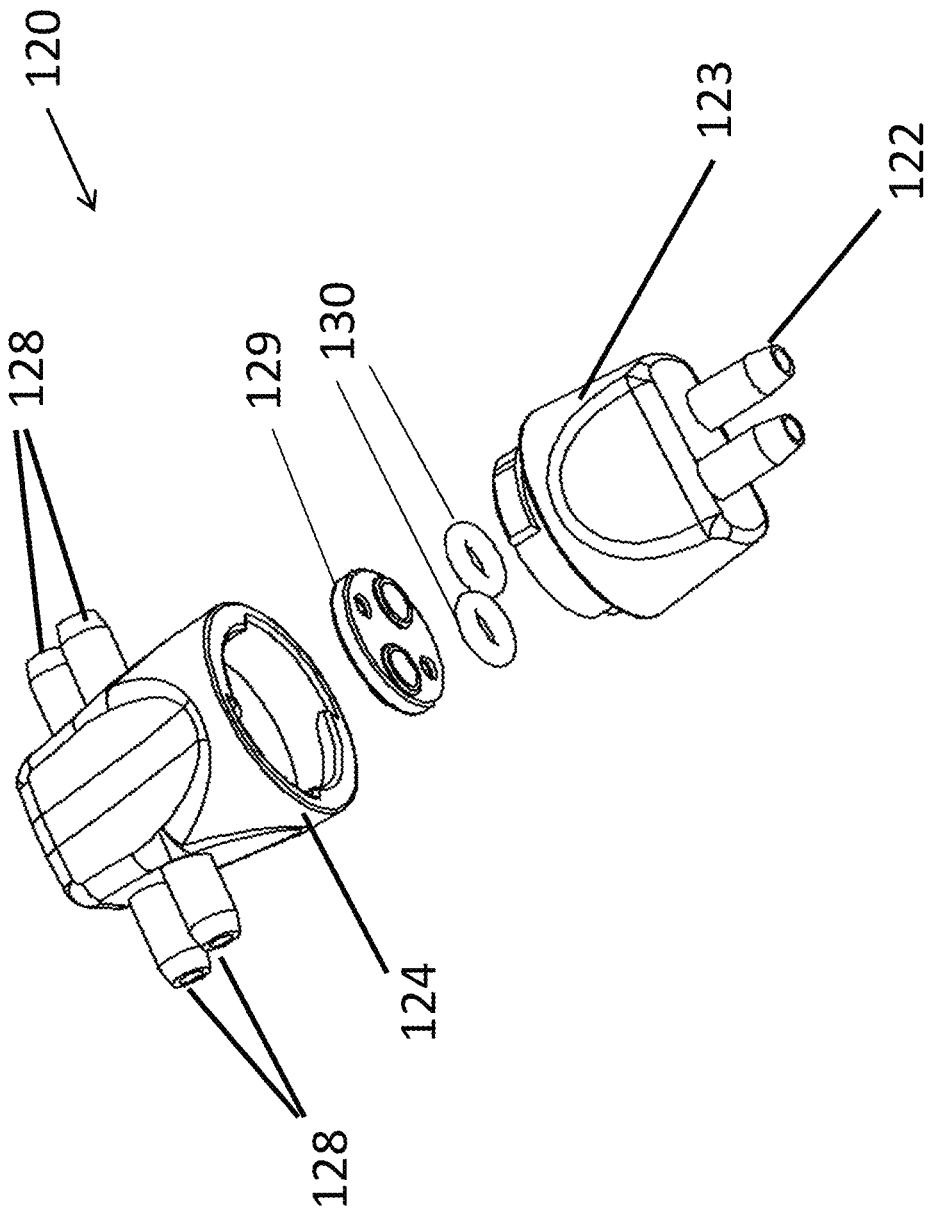
FIG. 11 shows an exploded view of connectors of the massage bra, according to an embodiment of the preset invention.

FIG. 11 illustrates exploded view of the connector parts according to an embodiment of the preset invention. The connector is comprised of a lower part 123 and upper part 124. The lower part has a double air inlet 122, which connects through tubes to the air pump unit 200. The upper part includes a pair of double air outlets 128 each pair connected to one side of the bra. Each outlet of the double outlet may be connected to a different bra tube, one to the inner tube, one to the outer tube. The air pump unit may be configured to control separately each tube, enabling the air pump unit to apply different inflating protocols. Within the connector are included O-ring seals 130 and elastic supports 129 for the O-ring seals.

Figure 12B:
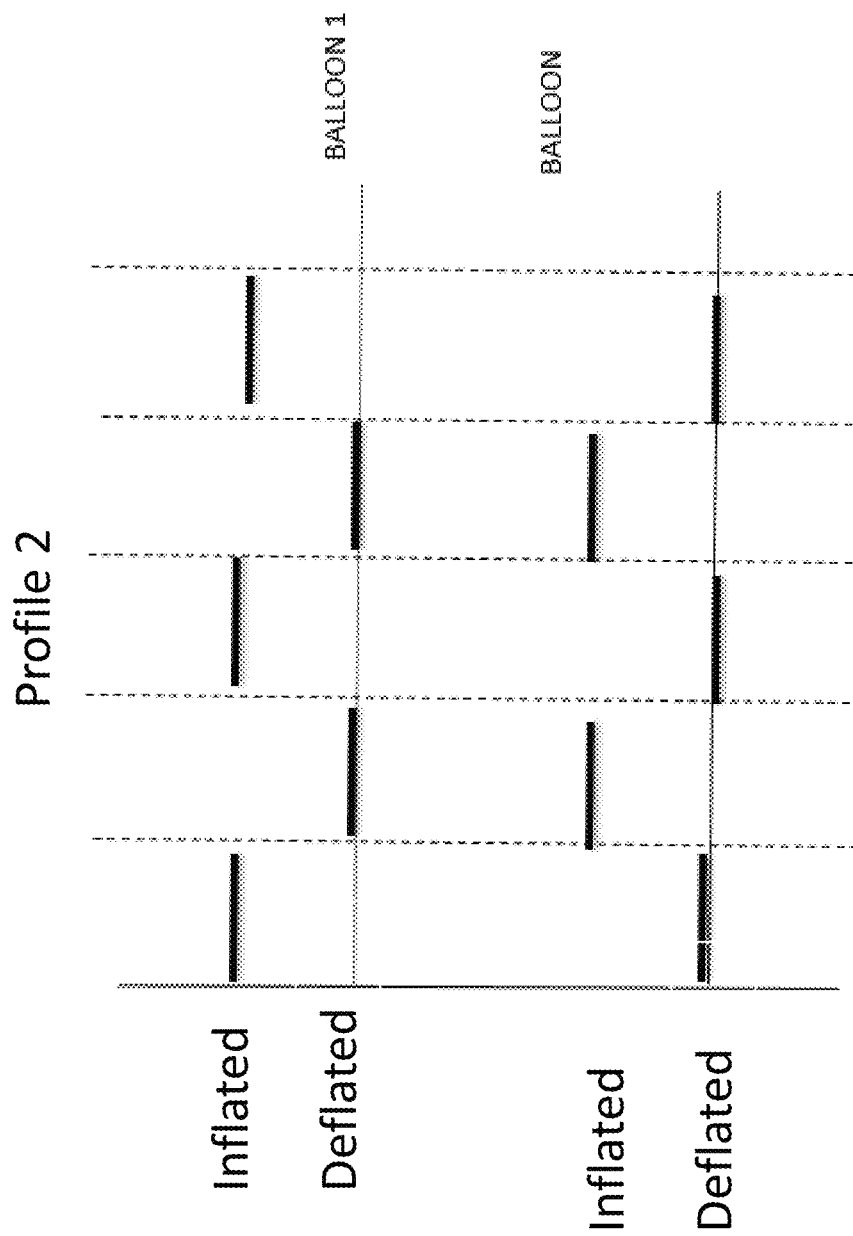
Figure 12C:
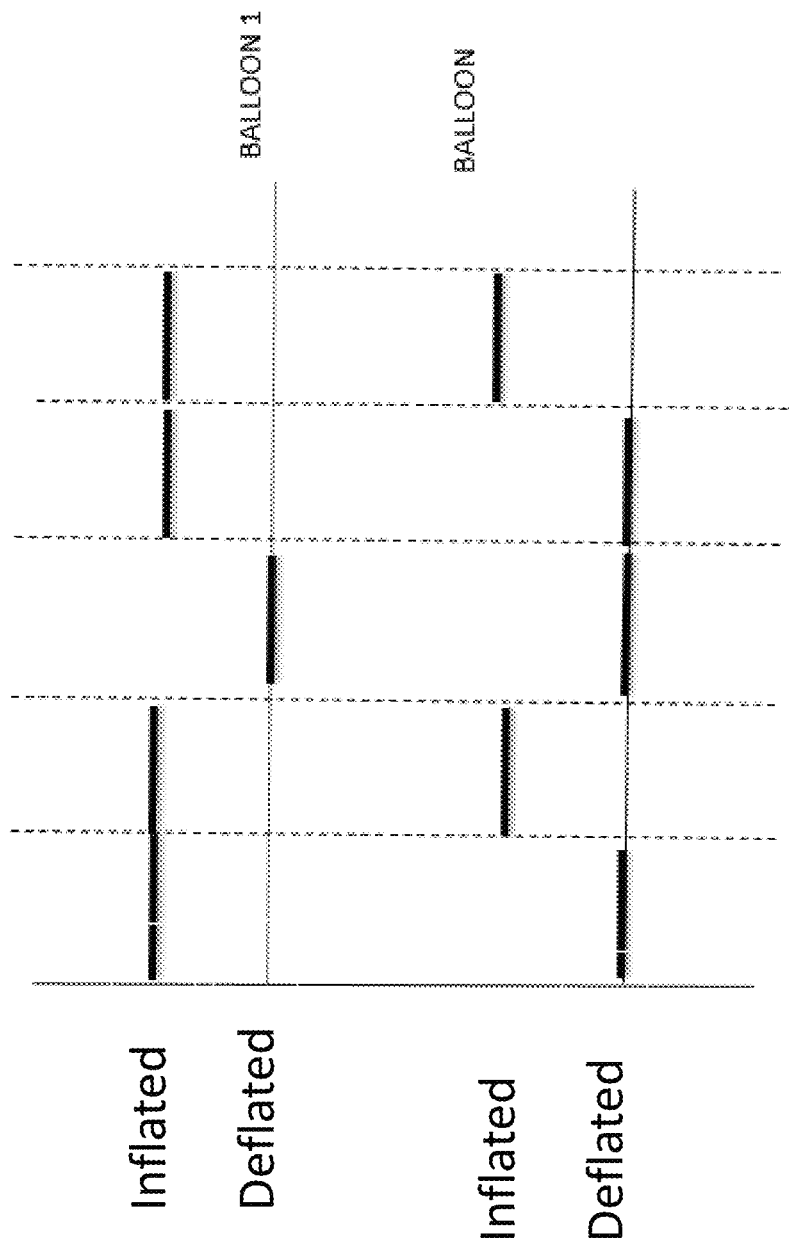

FIGS. 12A-12C illustrate profiles of patterns for inflating the tubes according to an embodiment of the preset invention. According to the FIG. 12A profile, the inner and outer balloons are activated together, in a timing sequence shown in the figure having equal inflation and deflation periods. The periods may be unequal in further embodiments. As shown in FIG. 12B, the inflation of the inner and outer balloons may be out of sync, or opposite. FIG. 12C illustrates a further sample protocol of inflating the tubes.

According to an embodiment of the current invention, contemporary operations of multiple functions of the massage bra 100 (e.g. applying massage pressure, heating, vibrating) is possible. Enabling the air pump unit to apply simultaneously, combination of different function of massage, vibration and heating at predefined timing, resulting different patterns of treatment.

It is to be understood that references in the specification or claims to an "additional" element does not preclude there being more than one of the additional element. It is also to be understood that where the claims or specification refer to "a" or "an" element, such reference is not to be construed as there necessarily being only one of that element. Where the specification states that a component, feature, structure, or characteristic "may", "might", "can" or "could" be included, that particular component, feature, structure, or characteristic is not required to be included.

The descriptions, examples, methods and materials presented in the claims and the specification are not to be construed as limiting but rather as illustrative only. The present invention may be implemented for the testing or in practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A massaging apparatus for a human breast, said apparatus comprising:

an air pump unit;

a bra having at least an inner inflatable tube and an outer inflatable tube, each having an air inlet, at each side of the bra and configured to encircle each breast, wherein each inflatable tube is connected by a connector connected to the air pump unit;

at least one biofeedback sensor located on the bra, wherein the biofeedback sensor is configured to measure directly a biologic parameter relating to a human body including one of: body temperature, heart rate, skin salinity; and a control module which controls the air pump unit for controlling speed and/or intensity of inflation of each of the inflatable tubes, wherein each tube is inflated at each of two ends of the tube creating dual simultaneous pressure configured to be applied at different locations of a breast organ;

wherein data collected by the at least one biofeedback sensor is transmitted to a computational module within the control module wherein the control module collects bio-feedback information from the at least one biofeedback sensor reflecting effectiveness of applied actions;

wherein the air pump unit is configured to provide movement similar to a sensation of a massage given by a human masseuse, and inflates, separately, each tube at different times according to a pre-defined protocol selected by the user in order to concentrate pressure to specific locations, wherein real time continuous biofeedback of sensor data reflecting effectiveness of applied massage actions, and determined according to the biologic parameter, is stored and displayed, and speed and/or intensity of inflation of the inner inflatable tube and the outer inflatable tube at each side of the bra are separately determined;

wherein all of the following predefined protocols are available to the user for selection:

a first profile, where the inner tubes and the outer tubes are activated together, having equal inflation and deflation periods, a second profile where the inflation and deflation periods are unequal;

a third profile where the inflation and deflation of the inner tubes and the outer tubes are out of sync, and exactly opposite to each other;

and wherein the connector is comprised of a lower part and an upper part, wherein the lower part has a double air inlet, which connects to the air pump unit via tubes, and the upper part includes a pair of double air outlets, each pair connected to one side of the bra, wherein each outlet of the pair of double air outlets is connected to a different bra tube, one of each pair to the inner tube of each respective side of the bra, and one of each pair to the outer tube of each respective side of the bra, wherein the air pump unit is configured to control each tube separately, enabling the air pump unit to apply different inflating protocols, wherein within the connector are included two O-ring seals and an elastic support interfacing with the two O-ring seals and having two holes corresponding to the O-ring seals, wherein the elastic support has a disk shape corresponding to an interior of the connector, the elastic support elastically supporting the O-ring seals interfacing with the two holes of the elastic support.

2. The massaging apparatus of claim 1, wherein a first part of each inflatable tube is relatively thicker than a second part.

3. The massaging apparatus of claim 1, wherein the air pump unit concentrates pressure to specific locations by inflating each inflatable tube separately.

4. The massaging apparatus of claim 1, further comprising heating elements comprising conductive wires in the bra, and wherein the air pump unit includes output interfaces to electric wires that convey electric power to said heating elements.

5. The massaging apparatus of claim 1, wherein vibration elements are embedded in the bra and the air pump unit includes output interfaces to electric wires that convey electric power to said vibration elements.

6. The massaging apparatus of claim of claim 1, wherein the air pump unit simultaneously applies a combination of functions of massage, vibration and heating at predefined timing periods.

7. The massaging apparatus of claim 1, wherein part of the inflatable tubes have a restricting film, wherein said restricting film prevents the inflatable tube from expanding in an isotropic manner.

8. The massaging apparatus of claim 7, wherein rings of a restricting film are spaced around a circumference of each inflatable tube.

9. The massaging apparatus of claim 1, wherein the connector includes two air inlets connected to the air pump unit and two pairs of air outlets connected to the outer inflatable tube and inner inflatable tube, enabling the air pump unit to inflate each of the inflatable tubes separately according to a pre-defined protocol.

* * * * *